United States Patent [19]

Lindstrom

[11] Patent Number: 5,558,653
[45] Date of Patent: Sep. 24, 1996

[54] TARGETED EYE DROP DISPENSER

[76] Inventor: Richard L. Lindstrom, 2811 Westwood Rd., Wayzata, Minn. 55391

[21] Appl. No.: 484,073
[22] Filed: Jun. 7, 1995
[51] Int. Cl.$^6$ .............................. A61M 35/00; B65D 5/66
[52] U.S. Cl. ............................ 604/295; 604/300; 222/113
[58] Field of Search ................................... 604/295, 297, 604/298, 294, 300, 301; 222/113, 362, 192

[56] References Cited

U.S. PATENT DOCUMENTS 2,598,357  5/1992  Coleman .............................. 222/113
4,515,295  5/1985  Dougherty ............................. 222/113
4,550,866  11/1985  Moore ...................................... 50/294

Primary Examiner—David H. Willse
Assistant Examiner—David J. Cho
Attorney, Agent, or Firm—Hugh D. Jaeger

[57] ABSTRACT

Targeted eye drop dispenser having concentric target rings of highly colored material aligned over and about the dispensing orifice. Highly visible material target rings aid in alignment of the dispensing orifice over the center of the human eye for self-dispensing of eye drops by the user of the targeted eye drop dispenser. An alternative embodiment includes a lighted target area.

2 Claims, 4 Drawing Sheets

TARGETED EYE DROP DISPENSER

CROSS REFERENCES TO CO-PENDING APPLICATIONS

None.

BACKGROUND OF THE INVENTION

1. Field of the Invention

The present invention pertains to medical liquid dispensers, and more particularly, pertains to an eye drop dispenser having a target zone at, or in very close proximity to the dispensing orifice. Target zones provide a focal point for the human eye so that self-administering of eye drops is accomplished with a greater degree of alignment accuracy.

2. Description of the Prior Art

Prior art devices have provided eye drop guidance systems in the form of dispensing tips which were merely colored or which had a ring on the tip surface and/or on the reservoir surface, which were on too large of a focal plane or which included focal planes which were distanced too far from each other.

The present invention provides a targeted eye drop dispenser having closely aligned target rings aligned about the dispensing orifice and lying together in a very close focal plane.

SUMMARY OF THE INVENTION

The present invention pertains to a targeted eye drop dispenser having a targeted area having concentric circles of highly visible colors aligned in a target fashion about the dispensing orifice. The highly visible target area provides a readily identifiable focal point for a person who is self-administering eye drops. The readily discernible target is visually focused upon to bring the dispenser in alignment with the eye, and at the same time, identifies the area of the dispensing orifice and helps differentiate between it and the remaining portion of the dispenser.

According to one embodiment of the present invention there is provided a targeted eye drop dispenser having a reservoir assembly and a cap. A threaded neck extends from the top surface of a reservoir bottle. A tubular extension member extends vertically from the upper region of the neck. A passageway, having an external dispensing orifice, aligns centrally along the axis of the tubular extension member. The top of the tubular extension includes a plurality of brightly colored concentric rings placed in a target fashion about the upper region of the tip.

An alternative embodiment discloses an eye drop dispenser having an illuminated target.

One significant aspect and feature of the present invention is a targeted eye drop dispenser.

Another significant aspect and feature of the present invention is a tubular extension member having concentric target rings.

A further significant aspect and feature of the present invention is concentric target rings which are highly colored.

An additional significant aspect and feature of the present invention is concentric target rings which are adjacent to one another and essentially on one plane.

Yet another significant aspect and feature of the present invention is concentric target rings which glow in the dark.

Yet a further significant aspect and feature of the present invention is an illuminated target zone area such as illumination by steady or flashing LEDs.

Still a further significant aspect and feature of the present invention is a target zone having a flashing LCD about the dispensing orifice.

Having thus described one embodiment of the present invention, it is a principal object hereof to provide a targeted eye drop dispenser.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
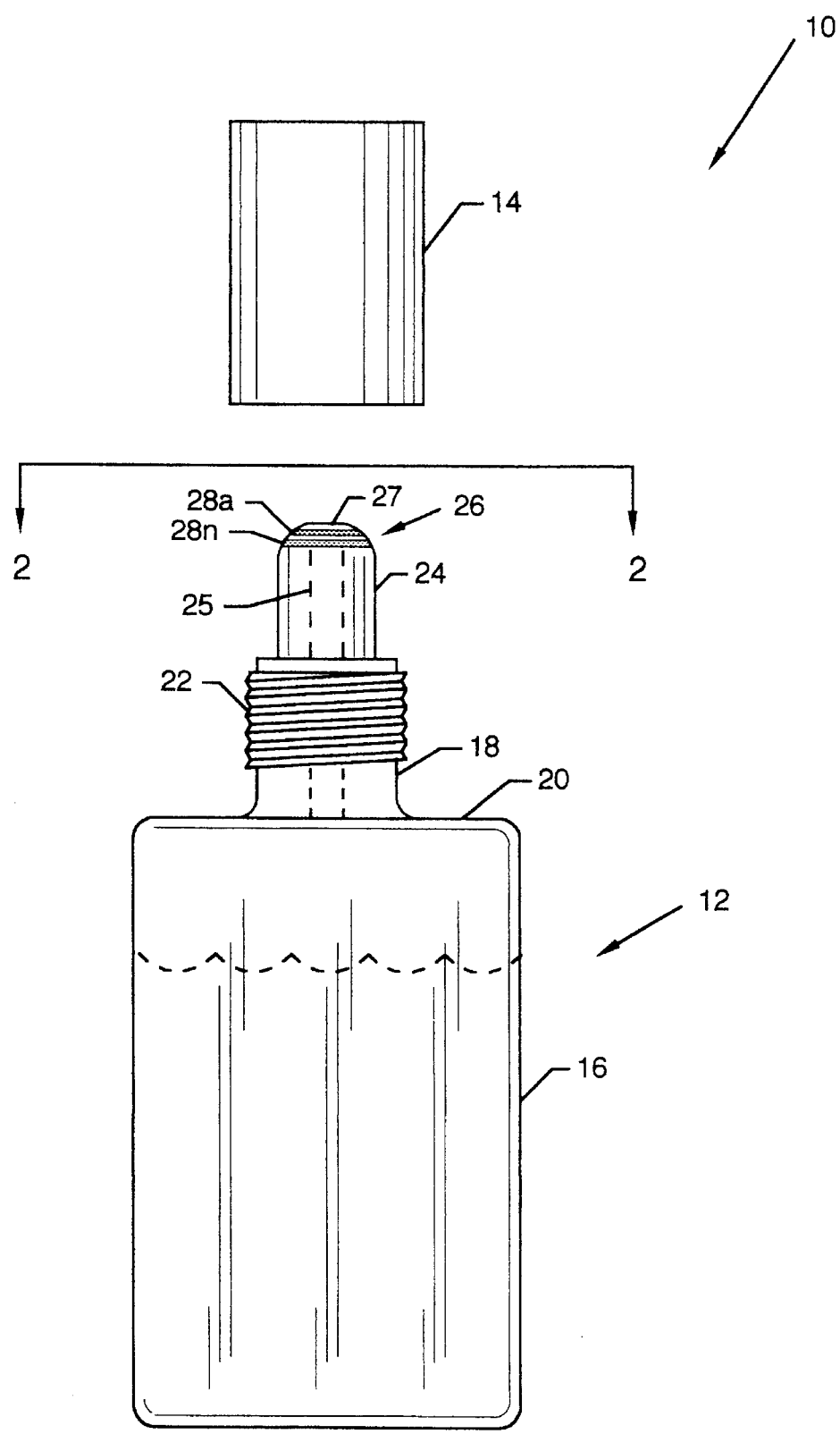
FIG. 1 illustrates an exploded side view of the targeted eye drop dispenser, the present invention.

FIG. 1 illustrates an exploded view of a targeted eye drop dispenser 10 including a reservoir assembly 12 and a cap 14. The reservoir assembly 12 includes a flexible plastic reservoir bottle 16, a neck 18 extending vertically from the top surface 20 of the reservoir bottle 16, a threaded surface 22 encompassing the neck 18, tubular extension member 24 extending from the neck 18, and a tubular passage 25 having a dispensing orifice 27 aligned in the tubular extension member 24. The tubular extension member 24 includes a target tip 26, which can be radiused as illustrated, and having a plurality of highly visible targets, such as rings 28a–28n aligned coaxially on the target tip 26. The target rings 28a–28n are of highly visible colors such as phosphorescent orange, lime or other suitable highly visible colors. Alternatively, the target tip 26 can include a flat surface or any other shaped surface suitable for bearing of a highly visible color, whether the colors are displayed in the form of concentric rings, a solid color, or any other suitable design which would lend itself toward visual capture during the process of eye drop application by an individual. The target tip 26 can also have target rings or surfaces which contain glow-in-the-dark visual surfaces for application in low light or complete darkness situations where a person's eyes cannot tolerate bright lights.

Figure 2:
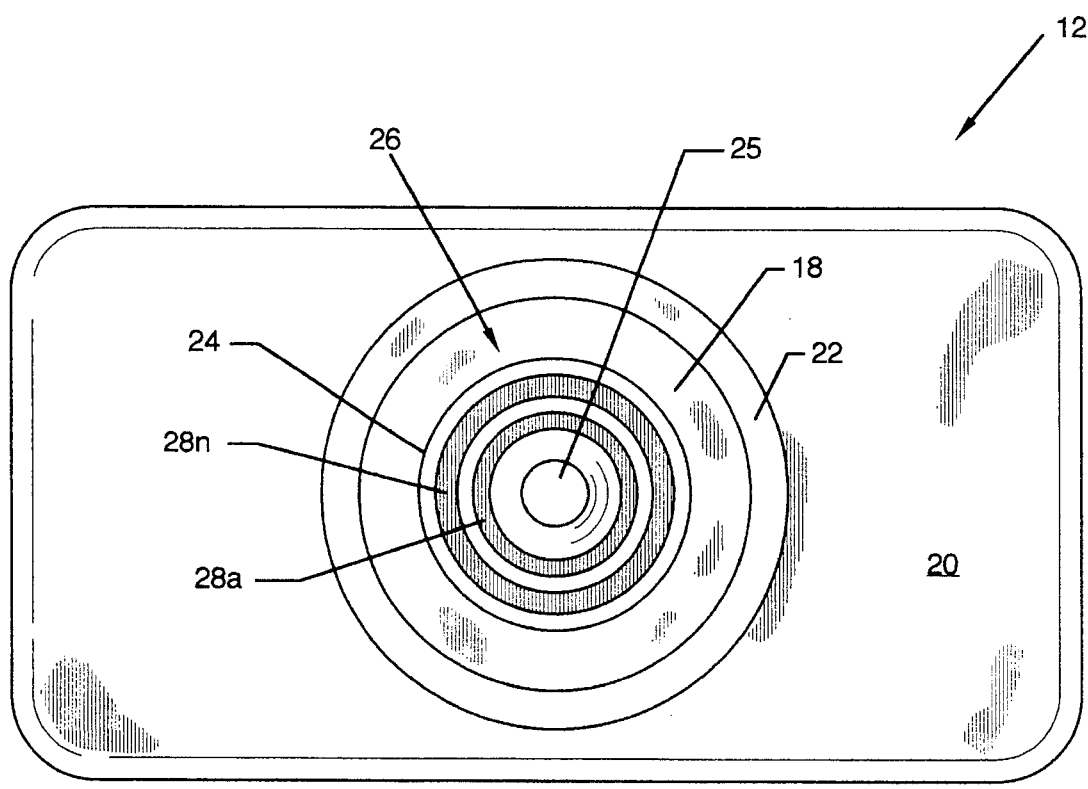
FIG. 2 illustrates a top view of the reservoir assembly along line 2—2 of FIG. 1.

FIG. 2 illustrates a top view of the reservoir assembly 12 along line 2—2 of FIG. 1 where all numerals correspond to those elements previously described. Illustrated in particular is the target tip 26 including the highly visible target rings 28a–28n.

Figure 3:
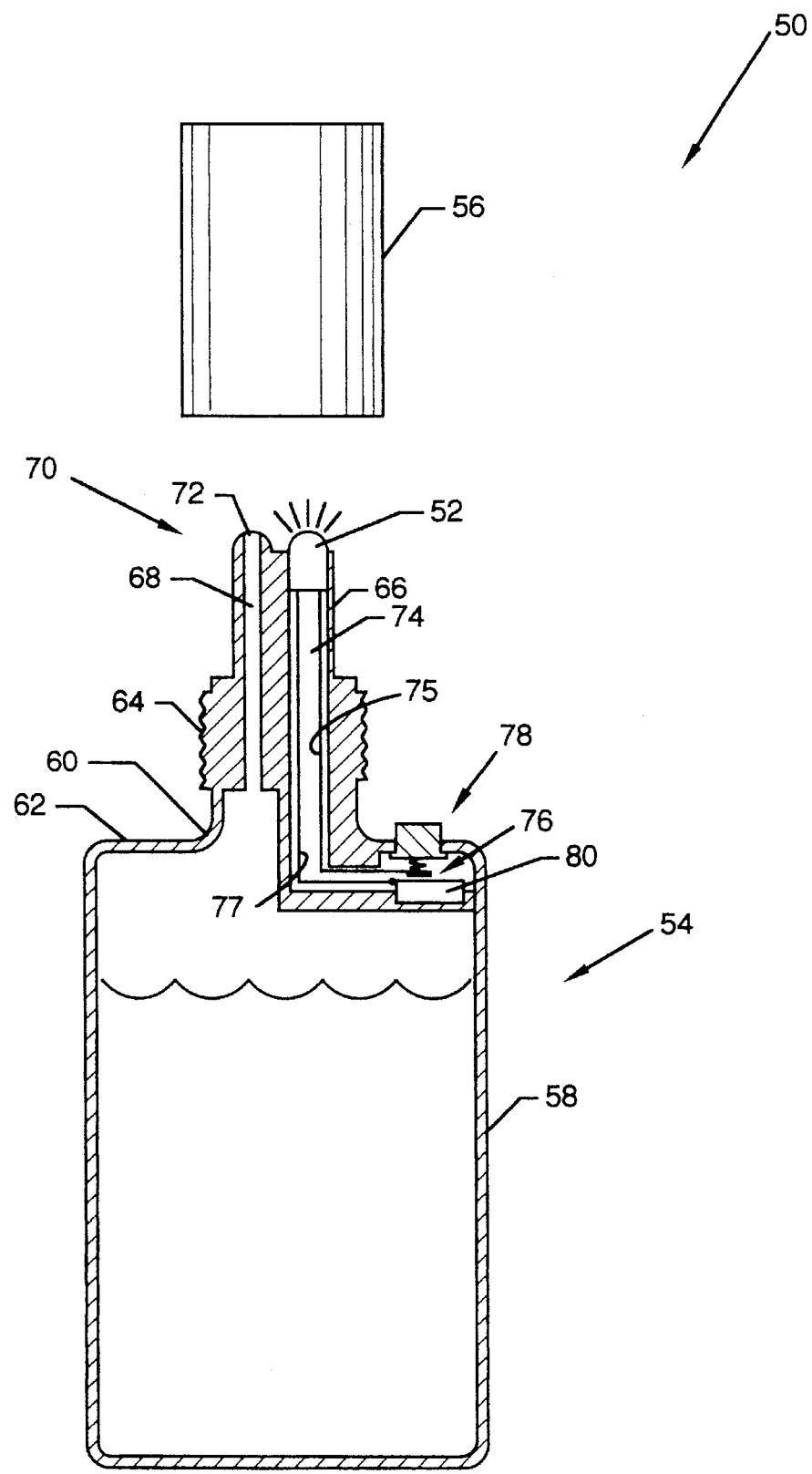
FIG. 3, an alternative embodiment, illustrates an exploded side view in cross section of a targeted eye drop dispenser having a lighted target; and, FIG. 4 illustrates the mode of operation of the targeted eye drop dispenser.

FIG. 3, an alternative embodiment, illustrates an exploded cross-sectional view of a targeted eye drop dispenser 50 having at least one or more lighted targets 52. The targeted eye drop dispenser 50 includes a reservoir assembly 54 and a cap 56. The reservoir assembly 54 includes a flexible plastic reservoir bottle 58, a neck 60 extending vertically from the top surface 62 of the reservoir bottle 58, a threaded surface 64 encompassing the neck 60, and a tubular extension member 66 extending from the neck 60. A tubular passage 68 in the neck 60 connects the interior of the reservoir bottle 58 and a target tip 70 to allow for dispensing of eye drop medication from the reservoir assembly 54. The lighted target 52, in the form of a light emitting diode (LED), aligns in the upper portion of the tubular extension member 66 at the target tip 70 in very close proximity to the dispensing orifice 72 at one end of the tubular passageway 68. The lighted target 52 aligns in a passageway 74 in the tubular extension member 66. Wires 75 and 77 from the lighted target 52 also align in the passageway 74 and connect to a switch assembly 76 actuated by a push button 78 and to a small battery 80 aligned in the structure of the reservoir bottle 58. The lighted target 52 can be in the form of a steady or pulsating LED of any desirable eye attracting color such as, but not limited to, white, red, green, yellow, or other desirable colors. In the alternative, the lighted target could be a lighted crystal display (LCD) which could be steady or pulsating. It is appreciated that an LCD could be applied in place of the plurality of target rings 28a–28n of FIG. 1, and flash sequentially from the outside ring to the inside ring, thus providing an eye catching target.

In another embodiment, the energy source, such as a battery for activating the lighted target, is placed in a separate carrier configured to receive at least a portion of the eye drop dispenser. Specifically, the battery is placed in the carrier with its leads exposed so that upon placing the dispenser in the carrier, the battery leads contact opposite leads on the dispenser that are in electrical communication with the light source. Preferably the carrier does not extend completely about the dispenser, in order that the reservoir remain partially exposed to enable squeezing of the same so as to dispense the eye drop solution. The carrier/dispenser combination can be constructed so that the light source always illuminates upon placing the dispenser in the carrier, or an additional switching mechanism such as that described previously can be used so that the dispenser can remain in the carrier without discharging the battery.

MODE OF OPERATION

Figure 4:
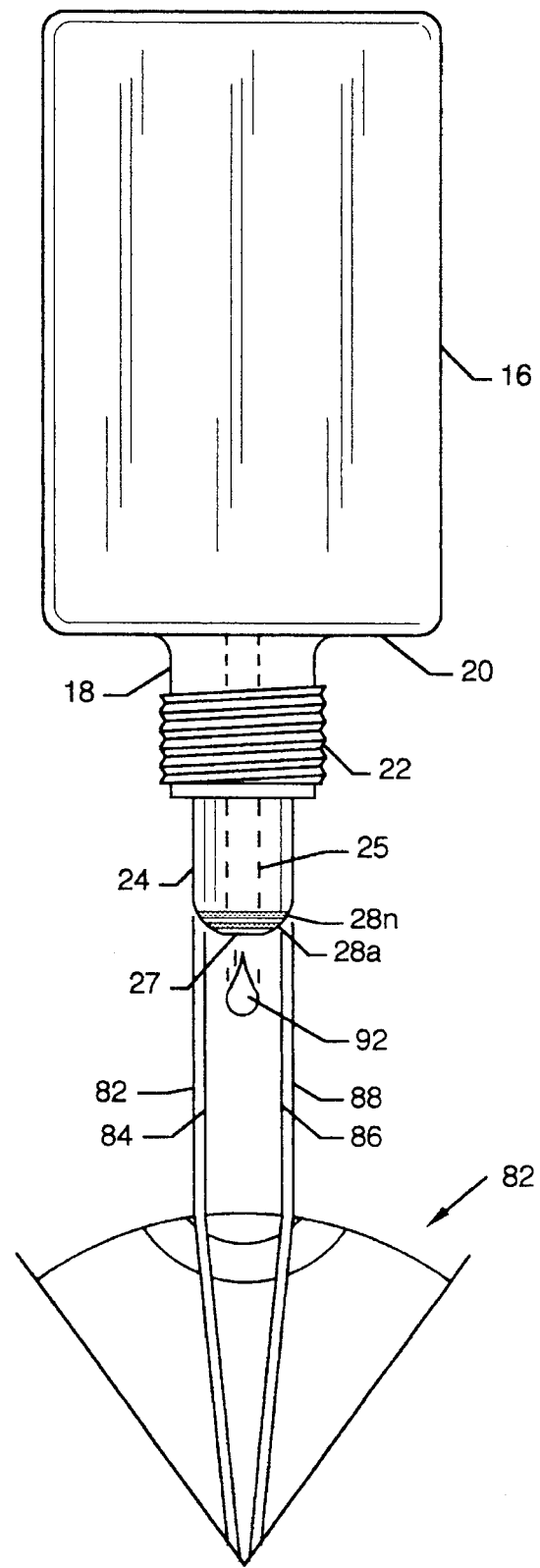

FIG. 4 illustrates the mode of operation of the targeted eye drop dispenser where all numerals correspond to those elements previously described. The cap 14 of FIG. 1 is first removed and then the reservoir assembly 12 is inverted by the user. The user then tilts their head back and the reservoir assembly 12 is placed in the region over the user's eye 82. The user then visually acquires the plurality of target rings 28a–28n and focuses upon them. After visual capture of the target rings, as portrayed by lines 82–88, the reservoir bottle is gently squeezed causing the desired eye wash solution 92 to be dispensed into the user's eye 82 from the aligned dispensing orifice 27.

Various modifications can be made to the present invention without departing from the apparent scope hereof.

I claim:

1. Targeted eye drop dispenser for dispensing eye drop solution into an eye, comprising:

a. reservoir means for containing said eye drop solution to be dispensed;

b. dispensing means extending from said reservoir means and in fluid communication therewith, said dispensing means having a dispensing orifice; and, c. visual target means associated with said dispensing means in proximity to said dispensing orifice, such that said eye drop solution can be accurately dispensed into said eye upon focusing said eye on said visual target means, wherein said dispensing means comprises a tubular extension member having a proximal end in fluid communication with said reservoir means and a distal end terminating in said dispensing orifice, wherein said visual target means comprises a light source at said distal end, and wherein said light source comprises a plurality of liquid crystal display concentric rings formed about said dispensing orifice.

2. Targeted eye drop dispenser for dispensing eye drop solution into an eye, comprising:

a. reservoir means for containing said eye drop solution to be dispensed;

b. dispensing means extending from said reservoir means and in fluid communication therewith, said dispensing means having a dispensing orifice; and, c. visual target means associated with said dispensing means in proximity to said dispensing orifice, such that said eye drop solution can be accurately dispensed into said eye upon focusing said eye on said visual target means, wherein said dispensing means comprises a tubular extension member having a proximal end in fluid communication with said reservoir means and a distal end terminating in said dispensing orifice, wherein said visual target means comprises a light source at said distal end, and wherein said light source comprises a plurality of liquid crystal display concentric rings formed about said dispensing orifice, wherein said plurality of liquid crystal display concentric rings comprises an inner ring about said dispensing orifice and an outer ring about said inner ring, and wherein said inner and outer ring are lighted sequentially.

\* \* \* \* \*